United States Patent [19]

Mount et al.

[11] Patent Number: 4,975,582

[45] Date of Patent: Dec. 4, 1990

[54] PRESSURE-MODULATED INFRARED GAS ANALYZER AND METHOD

[75] Inventors: Bruce E. Mount, Diamond Bar; Mark E. Koslin, Montclair, both of Calif.

[73] Assignee: Perkin-Elmer Corporation, Norwalk, Conn.

[21] Appl. No.: 324,069

[22] Filed: Mar. 16, 1989

[51] Int. Cl.⁵ .......................................... G01N 21/61
[52] U.S. Cl. ...................... 250/343; 250/345
[58] Field of Search .................. 250/345, 346, 343; 356/432 T

[56] References Cited

U.S. PATENT DOCUMENTS

| | | | |
|---|---|---|---|
| 3,005,097 | 10/1961 | Hummel | 250/345 |
| 3,728,540 | 4/1973 | Todd et al. | 250/343 |
| 3,902,068 | 8/1975 | Wood | 250/343 |
| 4,063,094 | 12/1977 | Schuman | 250/343 |
| 4,163,899 | 8/1979 | Burough | 250/343 |
| 4,188,534 | 2/1980 | Watanabe et al. | 250/345 |
| 4,468,561 | 8/1984 | Speeter | 250/345 |

Primary Examiner—Carolyn E. Fields

Attorney, Agent, or Firm—Thomas P. Murphy; Edwin T. Grimes

[57] ABSTRACT

A gas analyzer (10) for detecting low concentrations of a specific gas which has a sample chamber comprising passages (14, 30, and 32) through which radiant energy is directed and which is pressure modulated by a loud speaker (36) both of which provide a radiant energy signal which is detected by a beam splitter (82) having a measurement channel (86) directed to a measurement detector (92) and a reference channel (84) with a reference cell (94), containing gas of the type being analyzed, directed to a reference detector (90). Both detectors (92, 90) produce a signal, and these signals and a cross channel normalization constant are processed by an algorithm. The loudspeaker (36) is isolated from the sample chamber by a flexible diaphragm (42) to eliminate phase changes in the pressure modulated output of the loud speaker (36). Means are provided for measuring the modulation or AC pressure and the steady state or DC pressure in the sample chamber, the radiant energy modulation, the humidity in the sample chamber and the temperature of the analyzer as parameters for processing by the algorithm. Also disclosed is a method of detecting low concentration of a specific gas.

8 Claims, 2 Drawing Sheets (1 Hz)
SOURCE MOD.

DETECTOR OUTPUT
DUE TO SOURCE MOD.

DET. OUTPUT DUE TO
MOD OF SAMPLE (600 Hz)

TOTAL DET. OUTPUT

MEASUREMENT CHANNEL
OUTPUT SIGNAL VECTOR
DIAGRAM

REFERENCE CHANNEL
OUTPUT SIGNAL VECTOR
DIAGRAM

PRESSURE-MODULATED INFRARED GAS ANALYZER AND METHOD

BACKGROUND OF THE INVENTION

1. Field of Invention

This invention relates to gas analyzers for detecting low concentrations of a specific gas and is particularly directed to an improvement in such gas analyzers such that it is possible to detect low concentrations of a selected gas, carbon monoxide (CO), in the order of 5 parts per million (p.p.m.) in atmospheric air with a typical full scale capability of 130 p.p.m., over-ranging to as high as 400 p.p.m.

This invention also relates to a method of detecting low concentrations of a selected gas, such as CO.

2. Prior Art

The U.S. Pat. No. 4,163,899, entitled "Method & Apparatus for Gas Analysis" of I. G. Burough, discloses a pressure modulated infrared gas analyzer which utilizes an air pump as a pressure modulator pulsating through a sample chamber at a first frequency to produce modulation of the absorption of IR energy due to gas density changes, and modulation of the IR source intensity through said sample chamber at a second frequency to allow detection of IR source intensity changes.

This analyzer is used for the detection of CO with a full-scale sensitivity of approximately 3000 p.p.m. and resolution of approximately 100 p.p.m. which is 20 to 100 times less sensitive than the gas analyzer constructed in accordance with the teachings of this invention.

Inherent in the method and apparatus of the prior art gas analyzer is a limitation which prevents detection of levels of CO below about 50 to 100 p.p.m. With zero CO present in the sample chamber, an output equivalent to from 10 to 50 p.p.m. of CO is obtained; this may be referred to as an "offset". This offset may be due to several factors some of which are:

(1) Modulation of the IR energy due to vibration of the chamber walls, (2) Modulation of the IR energy due to the presence in the sample chamber of gases, such as carbon dioxide, which have energy absorption bands slightly overlapping that of the CO interference filter utilized, (3) Coupling of electrical energy from the pressure modulation source into the infrared detector circuitry (only a few microvolts is enough to produce several p.p.m. CO equivalent signal).

Suggestions have been made to improve the resolution of the prior art gas analyzer from 100 p.p.m. to 5 p.p.m. One suggestion was to use a catalytic CO removal cell after each measurement which was determined to be unacceptable for several reasons:

(a) the CO removal cell required an electro-mechanical valve to divert the sample into the removal cell. If four readings per minute are required on a continuous basis, the valve must cycle over two million times per year. By valving the sample gas containing CO through a catalytic CO removal cell, a reading of the offset may be obtained, and the offset subtracted from the reading obtained with the CO present in the sample. This procedure must be repeated each time a CO measurement is desired.

(b) a typical removal cell is constructed with a catalytic material which must be heated to provide optimum efficiency of CO removal. The energy required for heating the cell can be significant.

Another suggestion was to utilize a sample chamber which is resonant at the pressure modulation frequency, thus increasing the efficiency of the pressure modulation effect.

Another suggestion was to utilize a sample chamber with highly polished walls to act as a light guide, thus increasing the amount of modulated infrared received at the detector.

Both of these latter two suggestions were determined to be feasible but not adequate to achieve the sensitivity desired for a gas analyzer.

SUMMARY OF THE INVENTION

This invention improves the prior art gas analyzer by (a) incorporating a measurement channel and a continuous reference channel, (b) devising a reliable algorithm for calculating the gas concentration based upon the information available from the measurement and reference channels, and (c) incorporation of a flexible diaphragm between the pressure modulator and the sample chamber.

This invention also includes an improvement in the method of detecting low concentrations of a selected gas such as CO.

DETAILED DESCRIPTION

Figure 1:
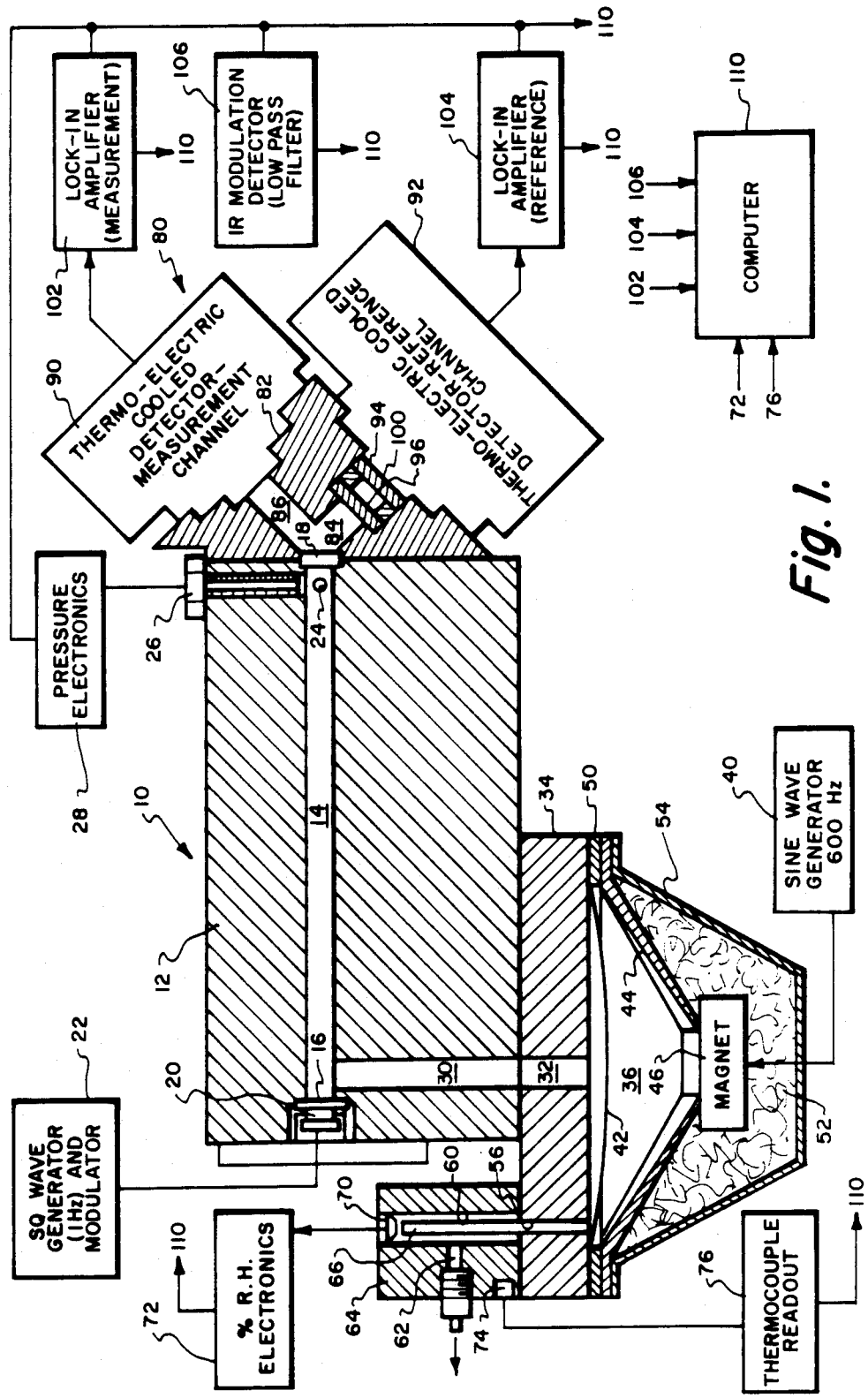
FIG. 1 is an elevational, cross-sectional, view of a gas analyzer constructed in accordance with the teachings of this invention and a schematic illustration of certain electronic circuitry used therewith.

As shown in FIG. 1, the gas analyzer of this invention, denoted in its entirety as 10, comprises a block shaped main body member 12 having a passage 14 which comprises passage 14 is closed at one end by a sapphire window 16 and at the other end by a 4.6 micron optical interference filter and sealing window 18. An IR source 20 is pulsed at the rate of 1 Hz by a square wave generator and modulator 22 and the wall of the passage 14 is highly polished so as to act as a light guide thus increasing the amount of modulated infrared energy reaching the sealing window 18. Within the closed part of the passage 14 and near the sealing window 18, a sample inlet port 24 is provided for a pressurized gas sample to enter the sample chamber and on this same end of the passage 14 and also within the closed part of the sample chamber is a pressure transducer 26 for converting pulsating pressure in the sample chamber into electrical signals communicating with suitable electronics 28.

In the area adjacent the sapphire window 16, the body member 12 is provided with a vertical passage 30 which communicates with the passage 14. The other end of the vertical passage 30 connects with a second passage 32 formed in a speaker plate 34 and thus connects the sample chamber with a loudspeaker 36 for providing the pulsating pressure through the two vertical passages 30 and 32 and the passage 14. The loudspeaker 36 is pulsed at the rate of approximately 600 Hz dependent upon the acoustic resonant frequency of passages 14, 30 and 32 by a sine wave generator 40. The passages 14, 30 and 32 comprise the sample chamber and their combined length is equal to one fourth of the acoustic wave length of the modulation frequency of the pulsating pressure in the sample chamber.

Interposed between the speaker 36 and the vertical passages 30 and 32 is a flexible modulator diaphragm 42 (typically of 2 mils thick nylon) isolating the air within the volume defined by speaker cone 44 and magnet 46 from the pulsating pressure in the sample chamber. A suitable seal ring gasket 50 is provided between the speaker plate 34 and the speaker 36.

In the prior art analyzer, there was no pressure isolation diaphragm, such as flexible diaphragm 42, between the loudspeaker and the sample chamber. Instead, the speaker was sealed inside a pressure chamber without sound absorbing material behind the speaker to eliminate acoustic reflections. The acoustic reflections from the back of the speaker contributed to phase instability in the voltage measured at the detector output.

The flexible diaphragm 42 of this invention allows atmospheric pressure to be present on both sides of the speaker cone 44. The higher pressure on the sample side of the flexible diaphragm 42, due to sample flow, maintains the tension necessary to transmit pressure oscillations from the loudspeaker 36 to the sample chamber which is typically at a frequency of 600 Hz. Radiated acoustic noise from the rear of the loudspeaker is attenuated by placing sound absorbing material 52 behind the loudspeaker 36 within a thin plastic chamber 54 which is not sealed against atmospheric pressure. The plastic chamber 54 is suitably attached to the loudspeaker 36. An additional benefit of the flexible diaphragm 42 is that phase changes due to changes in the effective length of the sample chamber (because variations in sample pressure due to variations in flow cause variable deflections of the modulator diaphragm) are eliminated. Eliminating this source of phase changes greatly stabilizes the offset voltage from the two detectors, reducing the rate of drift of the system calibration and lengthening the time between calibration cycles. Stated another way, with the flexible diaphragm 42, the speaker cone 44 and magnet 46 are free to operate independently of the pressure in the sample chamber and thus stabilize themselves in the positions for which they were designed.

On the same side of the diaphragm 42 as the sample chamber is a smaller vertical passage 56 in the speaker plate 34 coaxial with a second vertical passage 60 and a horizontal passage 62 in a block 64 which is smaller than the main body member 12. Passage 62 is the outlet for the gas sample. The vertical passages 56 and 60 contain a tube 66 connected to the sample chamber for flow of the sample gas therethrough which cooperates with a humidity sensor 70 to produce electrical signals corresponding to the humidity in the pressure chamber and which is connected to suitable electronics 72 to process such signals. The tube 66 is narrower than the passage 60 and forms a restriction for the flow of sample gas from the sample chamber thus maintaining the sample chamber at a slightly higher pressure than the atmospheric pressure as mentioned above.

The block 64 also contains a thermocouple 74 which is connected to suitable electronics 76 to produce a signal representative of the temperature of the analyzer.

On the same end of the main body 12 on the side of the sealing window 18 opposite the closed passage 14 is a detection assembly, denoted in its entirety as 80, which comprises a Y-shaped beam splitter 82 having two diverging cylindrical channels, a reference channel 84 and a measurement channel 86. These channels function as light guides and are highly polished for the maximum transfer of energy from the sealing window 18 to two detectors 90 and 92. The two channels are constructed as symmetrically as possible to cause the outputs of two detectors 90 and 92 to be identical with no CO present in the sample chamber. The two detectors 90 and 92 (lead selenide detector assemblies) are available from Andros, Inc of Berkeley, Calif., Model No. 80100.

The reference channel 84 contains a cylindrical sample cell 94 which is filled with CO as a reference gas. For a sample cell one-fourth inch in length, the cell is filled with 100% CO at 9 p.s.i. The interior surface of the sample cell 94 is of the same diameter as the reference channel 84, and is also highly polished, to allow maximum energy transmission through the sample cell. The sample cell windows 96 and 100, which seal the sample cell, are preferably of 0.5 mm thick silicon coated with a monomolecular layer of silicon monoxide to allow maximum transmission of IR energy (about 95%) therethrough. The sapphire, if a signal loss of 30% is allowable.

The output voltages from each of the two detectors 90 and 92, as shown in FIG. 2, consist of a combination of two frequencies: (1) a triangular wave of approximately 1 Hz and a few millivolts in amplitude (FIG. 2A), which is due to the 1 Hz square wave (FIG. 2A) modulation of the IR source 16, the triangular-shaped output being caused by the integration effect from the very slow temperature change of the source in response to the square wave change in current through the IR source 16, and (2) a sine wave comprising about 10 to 15 microvolts peak-to-peak of offset (both channels) (FIG. 2A), plus about 1 microvolt peak-to-peak per p.p.m. of CO (measurement channel only), at the frequency of the pressure modulation (typically 600 Hz) (FIG. 2C). The 600 Hz AC signals (FIG. 2C) are detectable using synchronous detectors 102 and 104 (sometimes called "lock-in amplifiers"), referenced to the AC output of the pressure transducer 26. The lock-in amplifiers 90 and 92 are available from E. G. & G, Princeton Applied Research Division, Princeton, N.J., Model No. 5210.

Derivation of CO concentration is accomplished by vectorially subtracting the offset voltage obtained from the reference channel 84 (the output due to CO being absorbed by the CO cell) from the output obtained from the measurement channel 86.

Figure 2A:
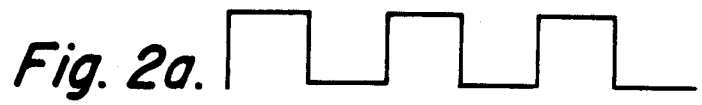
FIGS. 2a-f illustrate typical waveforms generated during the operation of a gas analyzer of this invention and accompanying vector analysis.
Figure 2B:
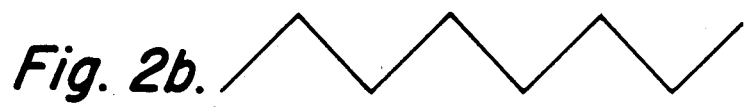
Figure 2C:
Figure 2D:
Figure 2E:
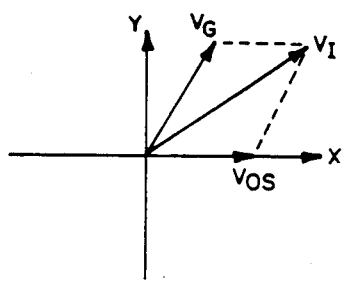
Figure 2F:
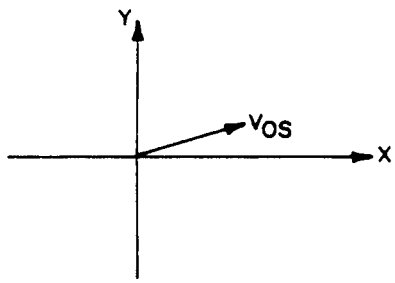

In FIGS. 2e and f, the vector $V_I$ (FIG. 2e) represents the output signal received from the measurement channel 86, which is the vector sum of offset vector $V_{OS}$ and absorption signal vector $V_G$. Vector rotation frequency is equal to the pressure modulation frequency. The output signal from the reference channel 84 (FIG. 2f) contains only the offset signal $V_{OS}$. The algorithm, Appendix A, calculates $V_G$ by subtracting vector $V_{OS}$ from vector $V_I$.

The measurement and reference channels 86, 84 have slightly different sensitivities due to optical path and electronic asymmetries. This produces slightly different values for Vos from each channel. To compensate for this effect, a sample gas is introduced into the analyzer which contains no carbon monoxide, so that the output of each channel will be due only to the offset component vector, $V_{OS}$. A cross-channel normalization constant may then be determined. In this manner, the offset vector $V_{OS}$ determined from the reference channel 84 may be multiplied by the appropriate constant such that it will exactly cancel the offset vector appearing in the measurement channel output.

Variations in DC pressure inside the sample chamber, modulation pressure, sample humidity, and analyzer temperature are measured and used to correct the final gas concentration reading. Variations in IR source intensity are detected by modulating the IR source intensity at a frequency much lower than the pressure modulation frequency. Source intensity variations may then be detected and electronically separated from the IR absorption signals at the pressure modulation frequency by an IR modulation detector (low pass filter) 106. The intensity variation information is used to provide a further correction to the gas concentration output. All necessary parameters being connected to computer 110.

A summary of all of the calculations required, including those used at the time of initial calibration and those used during each measurement, is given in Appendix A. The "Summary of Calculations" of Appendix A is the equivalent of a flow chart for the algorithm.

In the foregoing, CO is the gas being analyzed but other gases may be similarly analyzed with the gas in the reference cell changed accordingly. Similarly, the optical filter matches the IR energy absorption band for CO but if other gases are analyzed having different IR absorption bands of radiant energy are used, the filter will be changed accordingly. Also, "pump", "pressure modulator" and "speaker" are used herein interchangeably, and "IR energy" and "radiant energy" are used herein interchangeably.

We claim:

1. A gas analyzer for detecting the concentration of a selected gas in a gas sample, comprising,
    sample chamber means for containing a sample volume of the gas being detected,
    means for producing and directing radiant energy from a single source of radiant energy through the sample volume,
    means for modulating the power output of the radiant energy at a first frequency.
    pressure modulating means for modulating the sample volume at a second frequency,
    means for detecting the radiant energy and modulated pressure and producing a composite signal,
    said detecting means comprising means for splitting the detected radiant energy into two channels which guide one part of the detected radiant energy to a measurement detector which produces a measurement signal and which guides the second part of the detected radiant energy first through a reference cell containing a gas of the type being detected and then to a reference detector which produces a reference signal, and
    means for processing the measurement signal, the reference signal and a cross-channel normalization constant derived by processing a sample volume without the gas of the type to be detected to produce an output signal representative of the concentration of the gas in the sample volume.

2. The gas analyzer as claimed in claim 1 wherein said pressure modulating means comprises a loud speaker with a cone and magnet with means whereby said cone and magnet are isolated from he sample volume.

3. The gas analyzer as claimed in claim 2 wherein said isolating means comprises a flexible diaphragm.

4. The gas analyzer as claimed in claim 3 further including means for attenuating radiated acoustic noise in said loud speaker.

5. The gas analyzer as claimed in claim 4 wherein said sample chamber is one fourth of the wave length of the frequency of modulation of the pressure in the sample volume.

6. The gas analyzer as claimed in claim 5 wherein said sample chamber is highly polished for maximum energy transfer through said sample chamber.

7. A method for detecting the concentration of a selected gas in a gas sample, comprising,
    providing radiant energy from a single source.
    directing the radiant energy through the sample volume and modulating the power output of the radiant energy source at a first frequency,
    providing a pressure modulator connected to the gas sample,
    modulating the absorption of radiant energy within the sample volume by varying gas pressure at a second frequency,
    detecting the radiant energy passing through the sample volume and producing a reference signal and a measurement signal corresponding to the detected radiant energy by splitting the detected radiant energy into two parts by two guide channels and directing one part through a cell containing a gas of the type being detected and to a reference detector for providing a reference signal and directing the other part directly to a detector for providing a measurement signal, and
    processing said measurement signal and reference signal together with a known constant derived by processing a sample volume without the gas of the type to be detected to produce an output signal corresponding to the concentration of the selected gas in the sample.

8. A method for detecting the concentration of a selected gas in a gas sample, comprising the steps of:
    providing a single source of radiant energy,
    directing the radiant energy through the sample volume of gas having the selected gas of an unknown concentration and modulating the power output of the radiant energy source at a first frequency.
    providing a pressure modulator connected to the gas sample,
    modulating the absorption of radiant energy within the sample volume by varying gas pressure at a second frequency,
    detecting the radiant energy passing through the sample volume and producing a reference signal and a measurement signal corresponding to the detected radiant energy by splitting the detected radiant energy into two parts by two guide channels and directing one part through a cell containing a gas of the type being detected and to a reference detector for providing a reference signal and directing the other part directly to a detector for providing a measurement signal,
    introducing a cross-channel normalization constant previously derived from detecting a sample volume of gas having none of the gas to be detected by the same preceding steps in the method, and
    processing said measurement signal and reference signal together with the normalization constant to produce an output signal corresponding to the concentration of the selected gas in the gas sample volume.

* * * * *

UNITED STATES PATENT AND TRADEMARK OFFICE
CERTIFICATE OF CORRECTION

PATENT NO.   : 4,975,582
DATED        : December 4, 1990
INVENTOR(S)  : Mount et al It is certified that error appears in the above-identified patent and that said Letters Patent is hereby corrected as shown below:

Column 2, line 41, after "comprises", insert --both a light guide and part of a sample chamber. The--

Column 4, line 9, delete "80100" and insert --380100--

Column 4, line 21, after "The", insert --cell windows 96 and 100 may also be made of 0.5 mm--

Signed and Sealed this

Twenty-fifth Day of May, 1993

Attest:

MICHAEL K. KIRK

Attesting Officer

Acting Commissioner of Patents and Trademarks